(12) United States Patent
Brady

(10) Patent No.: US 7,755,351 B2
(45) Date of Patent: Jul. 13, 2010

(54) METHOD AND APPARATUS FOR DETECTING INCONSISTENCIES IN FIBER REINFORCED RESIN PARTS USING EDDY CURRENTS

(75) Inventor: Steven K. Brady, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/656,585

(22) Filed: Jan. 23, 2007

(65) Prior Publication Data

US 2008/0174306 A1   Jul. 24, 2008

(51) Int. Cl.
*G01N 27/90* (2006.01)
*G01R 33/16* (2006.01)
(52) U.S. Cl. ........................ 324/240; 324/222
(58) Field of Classification Search ............... 324/222, 324/228, 229, 234, 236, 239, 240, 243
See application file for complete search history.

(56) References Cited

U.S. PATENT DOCUMENTS

| 3,719,882 | A | * | 3/1973 | Pincus | 324/330 |
|---|---|---|---|---|---|
| 4,593,245 | A | * | 6/1986 | Viertl et al. | 324/238 |
| 4,639,669 | A | * | 1/1987 | Howard et al. | 324/239 |
| 4,706,020 | A | * | 11/1987 | Viertl et al. | 324/238 |
| 4,891,591 | A | * | 1/1990 | Johnston et al. | 324/234 |
| 5,028,100 | A | * | 7/1991 | Valleau et al. | 324/232 |
| 5,036,285 | A | * | 7/1991 | Shaw | 324/546 |
| 5,119,022 | A | * | 6/1992 | Kranbuehl et al. | 324/234 |
| 5,142,228 | A | * | 8/1992 | Kingsbury | 324/230 |
| 5,420,507 | A | * | 5/1995 | Laskowski | 324/236 |
| RE36,979 | E | * | 12/2000 | Vernon et al. | 324/234 |
| 6,794,886 | B1 | * | 9/2004 | Chen et al. | 324/716 |
| 7,115,869 | B2 | | 10/2006 | Shelley et al. | |
| 7,241,630 | B2 | * | 7/2007 | Hawkins et al. | 436/526 |

OTHER PUBLICATIONS

PCT/US2008/051219, dated Jan. 16, 2008, International Search Report.
"Novel Non-destructive Technique to Assess the Degradation of Adhesively Bonded Composite Structures", P. Boinard, R.A. Pethrick, W.M. Banks, and R.L. Crane; Insight vol. 43 No. 3, pp. 159-162, Mar. 2001.
"Characterization of aged nitrile rubber elastomers by NMR spectroscopy and microimaging", Maciej Garbarczylc, Winfried Kuhn, Jacek Klinowski, and Stefan Jurga; © 2002 Elsevier Science Ltd, Polymer 43 (2002) 3169-3172.

* cited by examiner

*Primary Examiner*—Kenneth J Whittington
(74) *Attorney, Agent, or Firm*—Tung & Associates

(57) ABSTRACT

Inconsistencies in a reinforced resin matrix part are detected using an inductive coupling probe connected with or part of a tuned resonant circuit. An alternating magnetic field produced by the probe is coupled to the part and produces eddy currents in the part. Inconsistencies in the part result in changes in the complex impedance and/or resonance of the circuit which are detected by a network analyzer.

23 Claims, 2 Drawing Sheets

METHOD AND APPARATUS FOR DETECTING INCONSISTENCIES IN FIBER REINFORCED RESIN PARTS USING EDDY CURRENTS

TECHNICAL FIELD

This disclosure generally relates to nondestructive testing and inspection techniques, and deals more particularly with a method and apparatus for detecting inconsistencies in parts formed from fiber reinforced resins.

BACKGROUND

Composite material has a life cycle much like other materials. Inspection is part of the process used to track the condition of composite materials during its life cycle.

Inconsistencies in the resin of a composite structure may be difficult to detect using nondestructive testing without accompanying inconsistencies in the fibers of the composite. Inconsistencies in the resin of a composite structure may be caused by many sources including, but not limited to, exposure to high temperature for short time periods or moderate temperatures for long periods, lightning strikes and electrical arcing. Structures may also acquire inconsistencies due to the force of a physical impact.

At present, there are no approved nondestructive test methods to assess inconsistencies in the resin of composites, particularly thermally induced resin inconsistencies.

The alterations of the composite structures may not be visible to the human eye. For example, in order to determine whether a composite structure or part may have been subjected to excessive thermal loads, it was necessary to cut sample plugs or sections from regions of the structure or part suspected of having undergone alteration. The material samples were subjected to any of several testing techniques, such as thermal mechanical analysis (TMA) or differential scanning calorimetry (DSC). The removal of sample plugs for analysis was a time consuming and destructive process, which, in the case of commercial aircraft operations, increased maintenance costs and cycle times at maintenance facilities.

Accordingly, there is a need for a method and apparatus for nondestructively inspecting carbon fiber reinforced resin composite structures which overcome the problems discussed above. Embodiments of the disclosure are directed towards satisfying this need.

SUMMARY

In accordance with one embodiment, an apparatus is provided for detecting inconsistencies in a carbon fiber reinforced resin composite material. The apparatus may comprise a circuit including an inductive probe producing a magnetic field coupled with the material, and an analyzer for analyzing the response of the circuit to changes in the magnetic field resulting from the detection of inconsistencies in the composite material. The circuit may be a tuned resonant circuit which includes a variable capacitor for tuning the circuit. The inductive probe may include a flat inductive coil arranged in a plane generally parallel to a surface of the material, which can be passed over the surface in order to scan the material for inconsistencies. The apparatus may further include means for applying an alternating signal to the circuit. The analyzer may analyze changes in at least one of the complex impedance and resonant frequency of the circuit.

In accordance with another embodiment, an apparatus is provided for detecting inconsistencies in a composite structure formed of multiple plies of carbon fiber reinforced resin. The apparatus may include an inductive coil for inducing eddy currents in the structure; means for applying an alternating electrical signal to the coil; a circuit coupled with the coil and having electrical characteristics that change in response to changes in the eddy currents; and, an analyzer for analyzing changes in the electrical characteristics of the circuit. The coil may be mounted within a housing that is movable over a surface of the structure. The circuit may comprise a tuned resonant circuit containing a variable circuit element for tuning the circuit.

In accordance with a further embodiment, a method is provided for detecting inconsistencies in a structure formed of carbon fiber reinforced resin material. The method may include the steps of generating an alternating magnetic field; producing eddy currents within the material using the generated magnetic field; inductively coupling to the eddy currents with an electrical circuit; and, analyzing changes in electrical characteristics of the circuit caused by changes in the eddy currents. The alternating signal may have a frequency between approximately 8 MHz and 18 MHz. Eddy currents are produced in the material by moving an inductive coil over the surface of the structure. The analyzed changes may include changes in the complex impedance of the circuit and/or changes in the resonant frequency of the circuit.

In accordance with still another embodiment, a method is provided of detecting inconsistencies in a resin part containing conductive reinforcement fibers. The method may include the steps of generating an alternating magnetic field; producing eddy currents in the part using the generated magnetic field; coupling the eddy currents with an LRC circuit; and, analyzing changes in characteristics of the LRC circuit resulting from changes in the eddy currents. The eddy currents may be produced by moving an inductive coil over a surface of the part, and the analyzed characteristics may include at least one of the capacitive reactance and the inductive reactance of the LRC circuit. The analyzed characteristics may further include measuring changes in the resonant frequency of the LRC circuit.

These and further features, aspects and advantages of the embodiments will become better understood with reference to the following illustrations, description and claims.

BRIEF DESCRIPTION OF THE ILLUSTRATIONS

DETAILED DESCRIPTION

Figure 1:
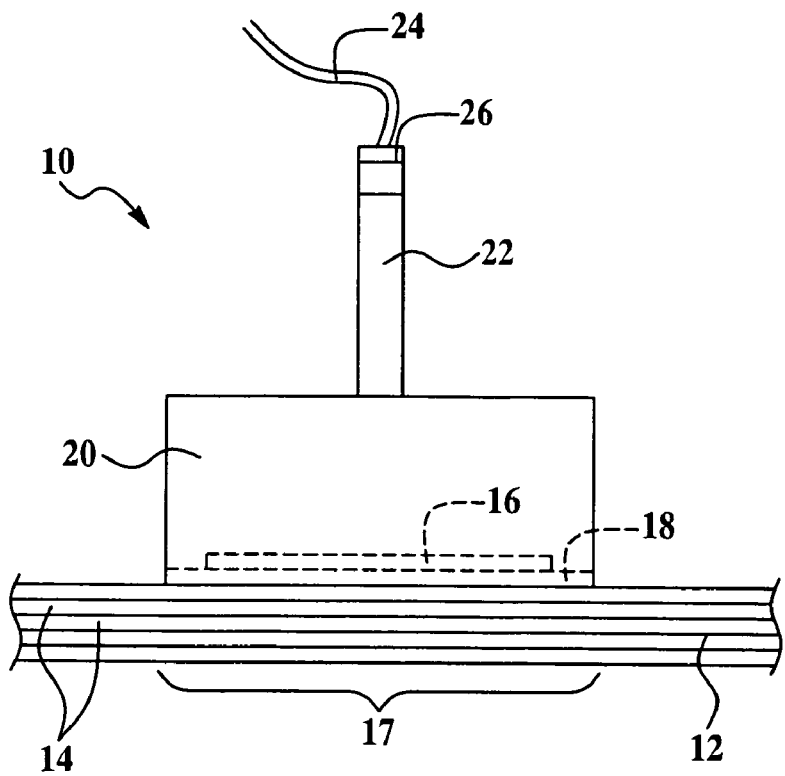
FIG. 1 is a side elevation illustration showing a probe contacting the surface of a carbon fiber reinforced resin structure.
Figure 2:
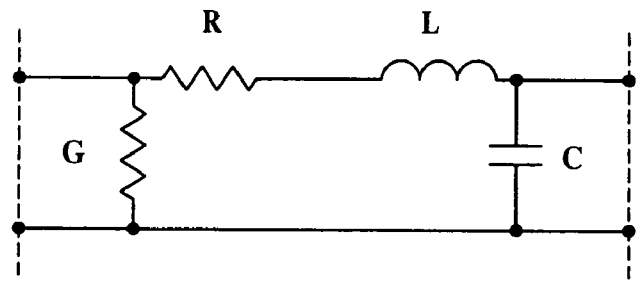
FIG. 2 illustrates a schematic circuit representing a transmission line model of the carbon fiber reinforced resin composite structure shown in FIG. 1.
Figure 3:
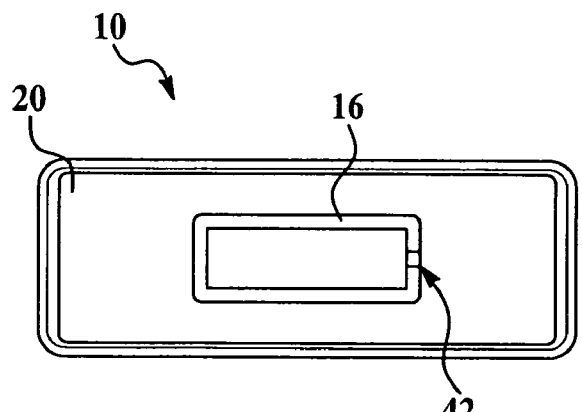
FIG. 3 is an illustration showing the bottom of the probe shown in FIG. 1.
Figure 4:
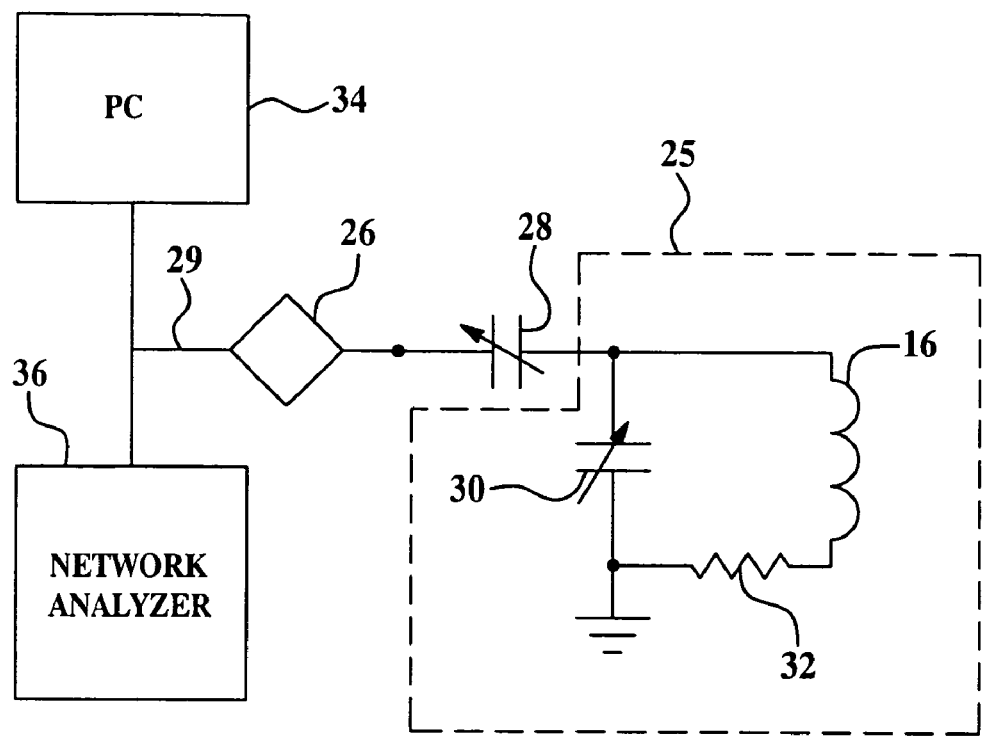
FIG. 4 is a combined block and schematic illustration of an apparatus for detecting consistencies in a composite structure according to an embodiment.

Referring first to FIGS. 1-4 a method and apparatus are provided for performing nondestructive inspection of a composite structure 12. The composite structure 12 may comprise a discrete part or a portion of a larger structure such as, but not limited to, a beam, a frame, a stringer, super-structure or skin of an aircraft.

The composite structure 12 may include a plurality of plies 14 of a fiber reinforced resin matrix in which the fiber reinforcement is a woven or knitted fabric of reinforcement fibers, or stranded fibers. The reinforcement fibers may be formed from electrically conductive material such as, without limitation, a carbon based material, and the resin matrix may comprise a synthetic resin such as, without limitation, epoxy. The composite structure 12 may be formed from quasi-isotropic lay-ups of the plies 14, in which each ply 14 has unidirectional fibers and successive plies 14 are rotated by defined amounts relative to each other. In a given ply 14, most of the reinforcing fibers are near to but not touching neighboring fibers, and are separated by a resin such as epoxy which is a dielectric (insulating) material.

When a local area of the structure 12 is subjected to an alternating magnetic field (i.e. having alternating north and south poles), eddy currents flow through the plies 14. The composite structure 12 has electrical characteristics that can be roughly modeled as a multi-conductor transmission line represented by the schematic circuit illustrated in FIG. 2. The transmission line model comprises four parameters: a series resistance R representing the resistance of the conductors; a shunt conductance G representing leakage of current through the dielectric between conductors; a series inductance L representing each conductor's self-inductance and inductance among the various conductors; and, a shunt capacitance C representing each conductor's self-capacitance and capacitance among the conductors. Applying this model to the composite structure 12, the low-resistance carbon fibers comprise the conductors in the model, and the epoxy resin comprises the insulating material between the conductors.

The composite structure 12 may contain any of a variety of inconsistencies in its constituent materials. These inconsistencies may include undesirable material properties, structural features or anomalies created at either the time of manufacture of the composite structure 12, or after the time of manufacture as a result of in-service operating conditions. "Inconsistencies" as the term is used in the appropriate context throughout this disclosure, refers to the difference between one or more measured characteristics of a composite structure that has been unaffected by exposure to external factors (including thermal loads, structural loads, oxidation, lightning, electrical arcing or physical impacts) or manufacturing anomalies with the same one or more measured characteristics of a composite structure that has been affected by exposure to the external factors or manufacturing anomalies.

The detection of inconsistencies may be of interest to maintenance personnel in determining whether certain parts of an aircraft may require rework or replacement of parts. In accordance with the present embodiment, inconsistencies may be detected using an inductive probe 10 to induce and measure the flow of electrical eddy currents in the plies 14 of the composite structure 12. As will be discussed below in more detail, the probe 10 functions as a resonator that is tuned to a particular inspection frequency, and is inductively coupled with the composite structure 12. The resonance characteristics of the probe 10 are therefore sensitive to the electrical impedance of the local section 17 of the composite structure 12 being inspected.

It has been found that the dielectric lossiness of the resin matrix in the structure 12 decreases monotonically with increasing thermal loading. Accordingly, the electrical impedance of the local section of the structure 12 being inspected, which depends in part on the resin's dielectric lossiness, changes smoothly with increasing severity of the inconsistency, which in turn causes the resonance characteristics of the probe 10 to vary smoothly with increasing severity of the inconsistency. In accordance with the disclosed embodiment, the resonance characteristics of the probe 10 are measured and then correlated to levels of severity of the inconsistency.

The response of the composite structure 12 to eddy currents induced by the probe 10 depends on the complex electrical impedance (Z) of the local section of the structure 12 being inspected. In general, the sample section may have electrical resistance, inductive reactance and capacitive reactance, all of which combine to determine the total, complex impedance Z. The eddy current probe 10 couples inductively with the sample section and its impedance is modified by the impedance of the sample. The impedance of the probe 10 determines the magnitude of the alternating current flowing in it and the phase of that current relative to the phase of the applied voltage. Changes in the impedance of the probe 10 which represent eddy current measurements may be displayed to an operator who is inspecting the structure 12 for inconsistencies.

In accordance with the disclosed embodiment, inconsistencies in the composite structure 12 such as those that may be caused by excessive and/or prolonged exposure to heat, increases the electrical resistivity, or alternatively decreases the dielectric lossiness of the epoxy resin matrix in the plies 14. The electrical permittivity ($\epsilon$) of the resin has been found to change non-monotonically with increasing severity of the inconsistencies induced by thermal loading, however in some systems this change may be relatively insignificant in determining the eddy current response. The electrical impedance Z of a sample section determines its eddy current response. Certain types of inconsistencies such as those caused by physical impact, may not alter the dielectric properties of the resin, but may alter the geometry of the local section of the structure 12 being inspected. Inconsistencies for example, may alter local geometry. The eddy current response depends upon the electrical impedance of the local section, which depends upon, among other parameters, the mutual inductance and capacitance of the fibers in the section, which in turn depend upon the fibers' geometry. Consequently, inconsistencies for example, may also be detected.

The probe 10, shown in FIG. 1, includes an outer housing 20 formed of rigid material such as aluminum having a tube like handle 22. The circuit 25 shown in FIG. 4, which includes the inductive coil 16 (FIGS. 2, 3, 4), is contained within the housing 20. The inductive coil 16 is mounted on the backside of a protective glass panel 18 which is secured to the housing 20, near the lower edges thereof. In one embodiment, the inductive coil 16 comprises a single loop having a gap 42 (FIG. 3) across which there is connected a variable capacitor 30 shown in FIG. 4. The variable capacitor 30 allows tuning of the circuit 25 and is connected in series with the inductive coil 16 and a lumped resistance 32 which comprises the resistance inherent in the conductors, the tuning capacitor 30 and the inductive coil 16. A variable coupling capacitor 28, a shown in FIG. 4, couples the circuit 25 through a BNC connector 26 and coax cable 29 to both a computer such as the personal computer 34 and a network analyzer 36. A variable coupling inductor (not shown) may be used in lieu of the variable capacitor 30. Capacitor 30 along with resistance 32 and the coil 16 form an LRC resonant circuit whose resonant frequency can be tuned using the variable tuning capacitor 30.

Network analyzer 36 may comprise a commercially available device such as, without limitation, a Hewlett Packard 8505A or 8753A network analyzer. The network analyzer 36 produces an AC signal that is applied through the inductive coil 16 to the sample section of the structure 12. Frequencies of the AC signal from about 8 MHz to 18 MHz produced by the network analyzer 36 which are applied to a sample section 17 (FIG. 1) have been shown to yield acceptable results, although frequencies above or below this range may be used. The inductive coil 16 generates a magnetic field which penetrates the sample section 17 and results in the flow of eddy currents in the plies 14.

As previously discussed, inconsistencies present in the composite structure 12, and particularly the sample section 17 result in increases in the electrical resistivity, and decreases in the dielectric lossiness of the epoxy resin matrix. Thus, the impedance of the resin in the area of the sample section 17 changes the flow of eddy currents. Changes in the eddy current flow are inductively coupled with the circuit 25, thereby altering the response of circuit 25. This altered response, which reflects potential inconsistencies in the composite structure 12, is reflected as a change in the resonant frequency of the circuit 25 and/or a change in the impedance of circuit 25. In either event, the network analyzer 36 senses changes in impedance and/or the resonant frequency of circuit 25 and displays this information to an operator. The signal applied to the sample sections 17 as well as the detected results may be recorded and stored in the PC 34.

Figure 5:
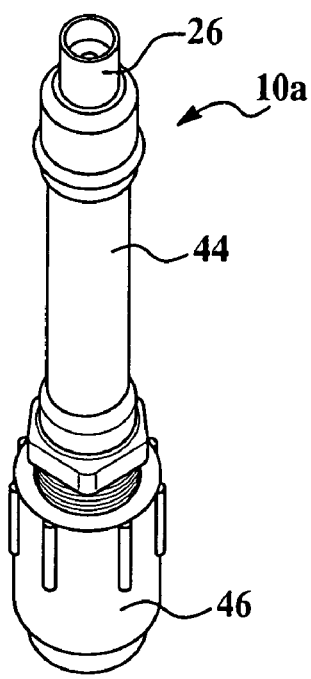
FIG. 5 is a perspective illustration of another embodiment of the probe.
Figure 6:
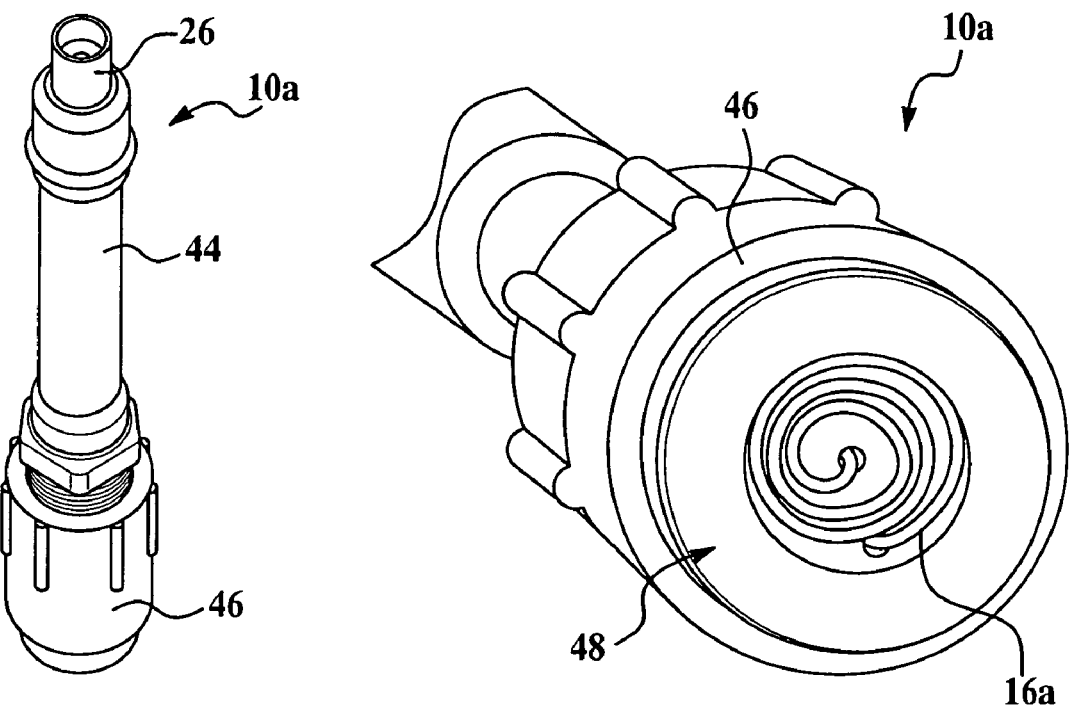
FIG. 6 is a perspective illustration of the base of the probe shown in FIG. 5.

An alternate embodiment of a probe 10a is shown in FIGS. 5 and 6. Probe 10a includes a cylindrical body 44 formed of conductive material such as, but not limited to copper, and a base 46 formed of an insulating material such as, without limitation, ceramic. A BNC connector 26 is connected on one end of the body 44 to allow the probe 10a to be connected with the network analyzer 36. The bottom of the base 46 includes a flat face 48 having a recess in which there is contained a flat spiral coil 16a. The coil 16a may be embedded in a protective encapsulation if desired.

In use, the probe 10a is moved across the surface of the structure 12 so that the magnetic field generated by the coil 16a produces eddy currents in various sample sections 17 of the structure. As previously described, changes in the eddy currents from sample section 17 to sample section 17 result in a change in the impedance and/or resonant frequency of the detection circuit 25. These changes in electrical characteristics are analyzed, recorded and displayed by the network analyzer 36. Frequencies of the AC signal from about 8 MHz to 18 MHz produced by the network analyzer 36 which are applied to the sample section 17, however, as previously stated, frequencies above or below this range may be successfully used.

It should be noted here that although an inductive probe 10, 10a has been specifically illustrated as a means for generating the magnetic within the structure 12, other arrangements for producing this magnetic field are possible. For example, the structure 12 could be placed within or moved through the magnetic field produced by a large inductive coil (not shown), such as that used in a solenoid.

The data analyzed and recorded by the network analyzer 36 may comprise an $S_{11}$ scattering parameter, which is a one port, reflected wave measurement. These $S_{11}$ measurements reveal changes in the electrical impedance of the probe 10a caused by inconsistencies in the sample section 17 as previously described. The network analyzer 36 measures changes in the $S_{11}$ magnitude and phase at a particular frequency which are indicative of possible inconsistencies in the structure 12.

Although the embodiments of this disclosure have been described with respect to certain exemplary embodiments, it is to be understood that the specific embodiments are for purposes of illustration and not limitation, as other variations will occur to those of skill in the art.

What is claimed is:

1. Apparatus for detecting localized inconsistencies in a composite material, comprising:
   a circuit including an inductive probe producing a magnetic field coupled to the composite material;
   means for applying an alternating electrical signal to the inductive probe; and,
   an analyzer for analyzing the response of the circuit to changes in the magnetic field resulting from said localized inconsistencies including determining changes in dielectric lossiness in the composite material resin matrix, said inductive probe adapted to move adjacent to a surface of said composite material surface to thereby generate eddy currents by said movement to detect said localized inconsistencies;
   wherein the circuit is a tunable LRC resonant circuit wherein a resonant frequency of said circuit may be tuned and wherein changes in said eddy currents are detectable by changes in said resonant frequency.

2. The apparatus of claim 1, further comprising a housing, and wherein the probe includes an inductive coil disposed within the housing.

3. The apparatus of claim 1, wherein the tunable resonant circuit includes a variable capacitor for tuning the resonant circuit.

4. The apparatus of claim 1, wherein the inductive probe includes a planar inductive coil arranged in a plane generally parallel to said surface of the composite material.

5. The apparatus of claim 1, further comprising means for applying an alternating signal to the circuit.

6. The apparatus of claim 1, wherein the analyzer analyzes changes in at least one of the complex impedance of the circuit and the resonant frequency of the circuit.

7. Apparatus for detecting localized inconsistencies in a carbon fiber reinforced resin composite structure, comprising:
   an inductive coil for inducing eddy currents in the composite structure, said inductive coil adapted to move adjacent to a surface of said composite structure to generate eddy currents to detect said localized inconsistencies, said detection of localized inconsistencies including determining changes in dielectric lossiness in a resin matrix of said composite structure;
   means for applying an alternating electrical signal to the coil;
   a circuit coupled with the coil and having electrical characteristics that change in response to changes in the eddy currents; and,
   an analyzer for analyzing changes in the electrical characteristics of the circuit including determining changes in dielectric lossiness in the composite material resin matrix, said changes produced by said inconsistencies;
   wherein the circuit is a tunable LRC resonant circuit wherein a resonant frequency of said circuit may be tuned and wherein changes in said eddy currents are detectable by changes in said resonant frequency.

8. The apparatus of claim 7, wherein the characteristics include at least one of complex impedance and resonant frequency.

9. The apparatus of claim 7, wherein the alternating signal has a frequency of between approximately 8 MHz and 18 MHZ.

10. The apparatus of claim 7, further comprising a housing, and wherein the coil is held within the housing over a surface of the composite structure through which the eddy currents are induced.

11. The apparatus of claim 7, wherein the tunable resonant circuit includes a variable circuit element for tuning the circuit.

12. A method of detecting localized inconsistencies in a structure formed of carbon fiber reinforced resin material, comprising the steps of:
(A) generating an alternating magnetic field;
(B) producing eddy currents within the material using the magnetic field generated in step (A), said eddy currents produced by moving an inductive coil and a surface of the structure relative to one another;
(C) inductively coupling the eddy currents with an electrical circuit; and,
(D) analyzing changes in electrical characteristics of the circuit caused by changes in the eddy currents, said eddy currents generated by moving said inductive coil and said surface of the structure relative to one another, said changes in the eddy currents caused by said localized inconsistencies, said analyzing including determining changes in dielectric lossiness in a resin matrix of said resin material;
wherein the circuit is a tunable LRC resonant circuit wherein a resonant frequency of said circuit may be tuned and wherein said changes in said eddy currents are detected by changes in said resonant frequency.

13. The method of claim 12, wherein:
step (B) includes passing the structure through the magnetic field produced by the inductive coil.

14. The method of claim 12, wherein step (D) includes analyzing changes in the complex impedance of the circuit.

15. The method of claim 12, wherein step (A) includes generating an alternating signal having a frequency between approximately 8 MHz and 18 MHz.

16. The method of claim 12, wherein step (B) includes moving said inductive coil over said surface of the structure.

17. The method of claim 12, wherein step (B) is performed by coupling the resin material to the magnetic field generated in step (A).

18. The method of claim 12, wherein step (D) includes analyzing changes in the resonant frequency of the circuit.

19. The method of claim 18 wherein:
step (B) includes passing the part through the magnetic field produced by the coil.

20. The method of claim 18, wherein step (D) includes measuring changes at least one of the capacitive reactance and the inductive reactance of the LRC circuit.

21. The method of claim 18, wherein step (D) includes measuring changes in the resonant frequency of the LRC circuit.

22. A method of detecting localized inconsistencies in a resin part containing conductive reinforcement fibers, comprising the steps of:
(A) generating a magnetic field having an alternating polarity;
(B) producing eddy currents in the part using the magnetic field generated in step (A), said eddy currents produced by moving an inductive coil and a surface of the part relative to one another;
(C) coupling the eddy currents produced in step (B) with an LRC circuit; and,
(D) analyzing changes in characteristics of the LRC circuit resulting from changes in the eddy currents, said eddy currents generated by moving said inductive coil and said surface of the structure relative to one another, said changes in the eddy currents caused by said localized inconsistencies, said analyzing including determining changes in dielectric lossiness in a resin matrix of said part;
wherein the LRC circuit is a tunable resonant circuit wherein a resonant frequency of said circuit may be tuned and wherein said changes in said eddy currents are detected by changes in said resonant frequency.

23. The method of claim 22, wherein step (B) includes moving said inductive coil over said surface of the part.

* * * * *